United States Patent [19]

Burzynski

[11] Patent Number: 4,470,970
[45] Date of Patent: Sep. 11, 1984

[54] PURIFIED ANTINEOPLASTON FRACTIONS AND METHODS OF TREATING NEOPLASTIC DISEASE

[76] Inventor: Stanislaw R. Burzynski, #5 Concord Cir., Houston, Tex. 77024

[21] Appl. No.: 330,383

[22] Filed: Dec. 15, 1981

Related U.S. Application Data

[63] Continuation-in-part of Ser. No. 279,728, Jul. 2, 1981, abandoned.

[51] Int. Cl.$^3$ .................... A61K 37/00; C07C 103/52; C07G 7/00
[52] U.S. Cl. ............................ 424/177; 260/112.5 R; 260/112 R
[58] Field of Search .................... 424/177; 260/112 R, 260/112.5 R

[56] References Cited
PUBLICATIONS

Chem. Abstr., vol. 95, (1981), 20593k.
Chem. Abstracts 14934(d), 1964.
Chem. Abstracts 63:7095(c), (1965).
Federation Proceedings Abstracts, 35:3, (Mar. 1, 1976).
International Cancer Research Data Bank, Abstract No. 183, (May 1, 1976).
Federation Proceedings Abstracts 32:3112, (Mar. 1973).
Lichtenstein, et al., "Antitumor Activity of Aromatic Acyl Derivatives of Amino Acids", Israel J. Med. Sci. 13:316, (1977).
Barbieri, et al., "Investigations on the Effect of Antitumor Peptides and Mixtures of Same", Estratto da Bollettino Chimico Farmaceutico 111:216, (1972).
Mardle, et al., "Reactive Acyl Dipeptides as Potential Penicillen Analogues. Part I. -(Acylaminosuccinimido)-Carboxylic Acids", J. Chem. Soc., 237–242, (1968).
Sheple et al., "The Fate of Some of the Phenyl-Acetylated Amino-Acids in the Animal Organism", J. Biol. Chem. 53:463–478, (1922).
Beall, et al., "Polypeptides that Inhibit Human Breast Cancer Cell Division", Cancer Biochem. Biophys. 3:93–96, (1979).

Burzynski, S. R., "Antyneoplastony", Pryeglad Lekarski 6:583–586, (1978).
Burzynski, et al., "Urinary Peptides Inhibit DNA Synthesis In Vitro in Certain Cultured Neoplastic Cells," Clinical Chemistry 23: 148–149, (1977).
Burzynski, et al., "Antineoplaston A in Cancer Therapy (I)", Physiol Chem. & Physics, 9: 485–500, (1977).
Burzynski, S. R. "Antineoplastons: Biochemical Defense Against Cancer", Physiol. Chem. & Phys. 8:275–279, (1976).
Gross, et al., "Urinary Peptides in Muscular Dystrophy", Physiol: Chem. & Phys. 8: 161–166, (1976).
Burzynski, et al., "Biologically Active Peptides in Human Urine: III. Inhibitors of the Growth of Human Leukemia, Osteosarcoma, and HELA Cells," Physiol. Chem. & Phys. 8:13–22, (1976).

(List continued on next page.)

Primary Examiner—Delbert R. Phillips
Attorney, Agent, or Firm—Arnold, White & Durkee

[57] ABSTRACT

Highly purified fractions from human urine exhibiting antineoplastic activity and processes for their preparation are described. The fractions comprise biologically active, small sized, low molecular weight peptides which exert cytostatic and cytotoxic activity toward neoplastic cell cultures and human neoplastic diseases. The fractions have been termed antineoplaston fractions. An antineoplastic active peptide common to each of the various antineoplaston fractions has been isolated and identified as 3-[N-phenylacetylaminopiperidine]-2, 6-dion. A synthetic mechanism for the preparation of 3-[N-phenylacetylaminopiperdine]-2, 6-dion is also disclosed, involving a combination reaction between L-glutamine and phenylacetyl chloride. Also disclosed are the hydrolysis degradation products of 3-[N-phenylacetylaminopiperidine]-2, 6-dion which also exhibit antineoplastic activity when administered according to the general teachings presented in this disclosure.

52 Claims, 5 Drawing Figures

PUBLICATIONS

Burzynski, et al., "Biologically Active Peptides in Human Urine: II. Effect of Intestinal Smooth Muscle and Heart," *Physiol. Chem. & Phys.* 6:457–468, (1974).

Burzynski, et al., "Biologically Active Peptides in Human Urine", *Physiol. Chem. & Phys.* 5:437–447, (1971).

Neish, W. J. P., "Phenylacetic Acid as a Potential Therapeutic Agent for the Treatment of Human Cancer", *Experientia* 27:860, (1971).

James, M., et al., "Conjugates of Phenylacetic Acid with Taurine and other Amino Acids in Various Species", *Proceedings of the Biochemical Society*, 124: 15P, (1971).

Hirom, et al., "Glutamine Conjugation of Phenylacetic Acid in the Ferret", *Biochemical Society Transactions*, 5:1033, (1977).

PURIFIED ANTINEOPLASTON FRACTIONS AND METHODS OF TREATING NEOPLASTIC DISEASE

This is a continuation in part application of parent application Ser. No. 279,728, filed July 2, 1981, now abandoned.

BACKGROUND OF THE INVENTION

The present invention relates generally to medicinal compositions and the use thereof; and more particularly, it relates to biologically active peptide compositions useful in the treatment of human neoplastic disease.

Investigations into the presence of physiologically or pathologically active peptides in urine have been on going for the past 80 years. Biologically active polypeptides have been isolated from urine which have demonstrated hormone like activity or regulation of biological function. Examples of biologically active polypeptide compositions isolated from urine include growth factors, pituitary hormones, and kinins.

The practically infinite variety of peptides that can be formed by the combination of the twenty common amino acids has prompted many investigators to suggest that peptides may constitute a system carrying information from cell to cell and organ to organ. Following this view on the regulatory significance of peptides, researchers have isolated urinary peptides which exert an influence on blood pressure, behavior modification, cardiovascular regulation, and smooth muscle activity.

Accordingly, it has been considered by a number of researchers that neoplastic growth may be controlled by naturally occurring biochemical defense mechanisms. The immunological process has most often been attributed with antineoplastic activity (see for example, Aoki et al, *Prog. Exp. Tumor Res.*, 19:23, 1974). There are, however, other possible mechanisms.

It has been suggested that neoplasia is a disease of cell differentiation. Given the large number of differentiating cells and assuming the possibility of error in the program for differentiation, groups of abnormally growing cells can often arise under the influence of carcinogenic factors. Without a reliable mechanism for "normalizing" such erroneously developed cells, the organisms would not live very long. Such a mechanism should be able to correct the growth of newly developed neoplastic cells and direct them into normal differentiation pathways. It is Applicant's belief that peptides are ideal compounds to function as information-carrying molecules regulating cell differentiation.

In recent years, Applicant has described a number of medium-sized peptides derived from human urine, which demonstrate inhibition of DNA synthesis and mitosis in cultures of various neoplastic cells without significant inhibition of normal cells replication [see Burzynski, *Physiol. Chem. Phys.*, 5:437 (1973); Burzynski et al, *Fed. Proc.*, 32:766 (1973); Burzynski et al, *Physiol. Chem. Phys.* 8:13 (1976); Burzynski et al, *Fed. Proc.* 35:623 (1976); Gross et al, *Physiol. Chem. Phys.*, 8:161 (1976); Gross et al, *Clin. Chem.* 23:148 (1977); Burzynski, *Physiol. Chem. Phys.*, 8:275 (1976); and Burzynski et al, *Physiol. Chem. Phys.* 9:485 (1977)].

The active compounds, but heretofore unidentified discrete compounds, from these fractions have been given the working name "antineoplastons". Applicant has defined antineoplastons as substances produced by a living organism that protect it against development of neoplastic growth by a nonimmunological process which does not significantly inhibit the growth of normal tissues.

Although some polypeptides have been synthesized which demonstrate antineoplastic properties, (see de Barbieri et al, *Boll. Chim. Farm.*, 111:216, 1972), Applicant is not aware of prior art describing small sized (less than 10 amino acids), low-molecular weight polypeptides which have been isolated and identified from tissues or body fluids that exhibit antineoplastic activity significantly higher than inhibition of normal cell growth. Nor is Applicant aware of prior art describing the peptide, 3-[N-phenylacetylaminopiperidine]-2, 6-dion, or its use as an antineoplastic agent.

SUMMARY OF THE INVENTION

In accordance with the present invention, low molecular weight substances (MW less than 2–5000) useful in the treatment of human neoplastic disease are isolated and concentrated from human urine. The isolation procedures involve initial ultrafiltration operations separating lower molecular weight compounds (less than 2000–5000 MW) from higher molecular weight compounds and proteins. Following the filtration and ultrafiltration operations, the resulting urine ultrafiltrate containing the lower molecular weight compounds is then subjected to diverse sequential separational procedure yielding in particular an antineoplaston fraction comprising small sized peptide compounds (less than 10 amino acids).

According to one sequential separational process, the urine ultrafiltrate is acidified, filtered again, and subjected to high performance liquid chromatography employing a silica gel C-18 column. The fraction detected and collected as refractive index peak after elution with 450 ml water is referred to as antineoplaston fraction A1.

According to a second sequential separation process, the urine ultrafiltrate is acidified, filtered again, and passed through a polymeric resin adsorbent column. Eluates are collected from the polymeric resin column corresponding to three sequential washes: water, water and methanol, and a final water wash. The combined eluates from these washes are acidified and then further purified by C-18 bonded phase silica gel chromatography. The colored fractions developed by a methanol wash are collected and combined to constitute antineoplaston fraction A2.

According to a third sequential separation process, the urine ultrafiltration is acidified, filtered again, adsorbed onto a polymeric resin adsorbent, and subsequently eluted from the resin with an alkaline solution. The alkaline eluate is acidified to pH 2.5 and then oxidized. The oxidized fraction is further purified to antineoplaston fraction A3 by adsorption chromatography on silica gel C-18.

According to a fourth sequential separation process, urine is first acidified and then oxidized. The oxidized solution is filtered and separated into antineoplaston fraction A4 by passage through silica gel C-18 chromatography phase. The colored fraction eluted with methanol is collected and termed antineoplaston fraction A4.

According to a fifth sequential separation process, the urine ultrafiltrate is acidified and then eluted from silica gel C-18 by a methanol wash. The colored portion of the methanolic eluate is collected and termed antineoplaston fraction A5.

Further in accordance with the present invention, the common component of each of the antineoplaston fractions was isolated to homogeneity using high performance liquid chromatography and thin layer chromatography. The common component of each antineoplaston fraction A1 to A5 was identified as 3-[N-phenylacetylaminopiperidine]-2, 6-dion.

Further in accordance with the present invention, a method for synthesizing the major active component, 3-[N-phenylacetylaminopiperidine]-2, 6-dion is provided, which comprises the steps of reacting L-glutamine and phenylacetyl chloride together followed by several extraction operations to isolate the product, 3-[N-phenylacetylaminopiperidine]-2, 6-dion, from by-products.

Upon hydrolysis of 3-[N-phenylacetylaminopiperidine]-2, 6-dion there are yielded the degradation products, phenylacetyl glutamine and phenylacetic acid.

The antineoplaston fractions, 3-[N-phenylacetylaminopiperidine]-2, 6-dion and degradation products are useful in the treatment of human neoplastic disease.

DESCRIPTION OF THE PREFERRED EMBODIMENTS

The invention will be described in terms of preferred embodiments known to the Applicant at the time of this application which represent the best mode corresponding to the isolation, purification and implementation of urine antineoplaston fractions and synthetic antineoplastons exhibiting antineoplastic activity.

In accordance with such preferred embodiments, starting material for the preparation of each antineoplaston fraction is urine pooled from healthy subjects. Typically, the amount of urine required to elaborate useful yields of a desired antineoplaston fraction A1–A5 range from about 2000–3000 liters. Usable yields extracted from 2000–3000 liters of urine are on the order of 100–800 grams of dry matter for each of the respective antineoplaston fractions. Pooled urine specimens may be lyophilized to a dry powdered form if the extraction, isolation and purification processes are not to be accomplished immediately. Typically, however, the isolation and purification of the respective antineoplaston fractions are performed immediately utilizing the freshly pooled urine.

It is to be noted that standard precautions against bacterial contamination are taken throughout and the preparations are routinely checked for pyrogenicity, toxicity and sterility assay according to standard techniques. Pyrogen free sterile water is employed throughout the final steps and all procedures are performed at ambient room temperature unless stated otherwise.

A. Isolation and Purification of Antineoplaston Fraction A1 From Human Urine Reconstituted lyophilized urine (redissolved in deionized or distilled water) or freshly pooled urine is first physically filtered through paper, membrane, or cartridge filter having an average pore size of $3\mu$. The first filtrate is then filtered through a second filter having an average pore size of $0.2\mu$. These filtering steps are performed to separate suspended particulate or sedimented matter from the urine fluid.

Next, the prefiltered urine is submitted to ultrafiltration. Desirably, ultrafiltration is accomplished through a hollow fiber system, preferably an Amicon or Romicon system filter having a molecular weight cut off of about 5000 daltons. For the purpose of ultrafiltration, any other ultrafiltration membrane or hollow fiber ultrafilter may be employed having a molecular weight cut off suitably in the range of 5000 to 2000. Such ultrafiltration serves to remove materials having molecular weights greater than 2000 to 5000 depending on the selected filter employed.

The ultrafiltrate is acidified with concentrated acid, suitably hydrochloric or sulfuric acid, added slowly while vigorously stirring until the solution reaches a pH ranging from 2 to 3, preferably pH 2.5. The acidified ultrafiltrate is then filtered through a $0.2\mu$ filter to remove any precipitated particulate matter.

High performance liquid chromatography techniques are used to further purify and concentrate the designated antineoplaston fraction A1. A sample, suitably 250 ml (the amount, of course, depends upon the capacity of the system), of the acidified ultrafiltrate is introduced into a high performance liquid chromatography column, desirably a Waters Prep 500 HPLC system utilizing a Prep 500 C-18 silica gel cartridge column (bonded phase type silica). The system is also equipped with a refractive index detector. However, any suitable means of detection such as UV photometry, ion detector, etc. is suitable. Antineoplaston fraction A1 is eluted with deionized or distilled water and is characterized as the component peptide fraction having a refractive index peak occurring after passage of approximately 450 ml of water through the column. The resulting antineoplaston fraction A1 is collected and concentrated by rotary evaporation under reduced pressure and then further freeze dried by lyophilization.

Antineoplaston fraction A1 can be used in a wide variety of pharmaceutical forms including, but not limited to, intravenous, intramuscular, subcutaneous, intracavital and intratumor injections, capsules and tablets for oral administration, rectal suppositories and solutions and sprays for topical use.

B. Isolation and Purification of Antineoplaston Fraction A2 from Human Urine Urine which has been prefiltered and ultrafiltered according to the description directed to the preparation of antineoplaston fraction A1 is acidified with concentrated acid, typically hydrochloric acid. The acid is added slowly to the ultrafiltrate solution while vigorously stirring until the solution reaches a pH ranging from about 1 to about 2, preferably pH 1.5.

The ultrafiltrate from the above step is introduced onto a chromatography column containing a polymeric resin adsorbent, preferably Amberlite XAD-8 polymeric resin adsorbent, a product of Rohm & Haas Co., Philadelphia, Pa. Any other material similar to chemical structure or physicochemical properties may be substituted for the Amberlite adsorbent. The active antineoplastic materials are eluted from the column by employing sequential washings comprising a first wash of deionized or reverse osmosis water (W1); a second wash of a mixture of water and methanol (for example, 8% volume/volume) (M); a third wash of deionized or reverse osmosis water (W2); a fourth wash of 4% sodium hydroxide aqueous solution (N); and a fifth wash of deionized or reverse osmosis water until the pH of the eluate is in the neutral range. Eluates W1, W2 and M are collected. The pH of the solutions of W1, W2 and M is adjusted to about 2.5 with dropwise addition of acid, for example sulfuric acid.

The eluates W1, W2 and M from the previous step are passed through a chromatographic column packed with silica gel prep C-18 (bonded phase type silica gel) available from Waters Associates, Whatman or other companies. The column is initially washed with deionized or distilled water and then eluted with methanol. Three brownish-yellow colored fractions appear as bands, designated MW1, MW2 and MM. Colored fractions MW1, MW2 and MM are collected independently and each fraction is concentrated on a circulatory evaporator to a 1 liter volume. Each fraction is further evaporated to dryness either by rotary evaporation or by freeze drying. Dry fractions MW1, MW2 and MM are suitable for pharmaceutical application separately or mixed together. The mixture of them is termed antineoplaston fraction A2, and the mixture is suitable for pharmaceutical administration in the same variety of formulations and routes of administration described for antineoplaston fraction A1.

C. Isolation and Purification of Antineoplaston Fraction A3 from Human Urine Antineoplaston fraction A3 is isolated from urine during the same operation as the isolation and purification of antineoplaston fraction A2. Prefiltration, ultrafiltration, acidification, XAD-8 adsorption and elution is identical to that practiced for the isolation of antineoplaston fraction A2.

Fraction N eluted from the XAD-8 column with 4% sodium hydroxide is collected and the pH is adjusted to 2.5 with acid, desirably sulfuric acid. Fraction N is then subjected to oxidation operations. The oxidation of fraction N is preferably accomplished by dropwise addition of a saturated aqueous solution of potassium permanganate until the violet color of potassium permanganate disappears.

After the oxidation operation, fraction N is filtered sequentially through a $3\mu$ and $0.2\mu$ filter and the clear filtrate is further separated by C-18 chromatography. This chromatographic step is repeated in the same manner as described for the isolation of antineoplaston fraction A2. The colored band visible on the column designated MN is eluted with methanol. The colored band MN is collected and evaporated to dryness or freeze dried. This fraction is called antineoplaston fraction A3 and is suitable for direct pharmaceutical application. Antineoplaston fraction A3 can be used in the same variety of pharmaceutical formulations and routes of administration as listed for antineoplaston fraction A1.

D. Isolation and Purification of Antineoplaston Fraction A4 from Human Urine The pH of reconstituted or fresh urine is adjusted to 2.5 with acid, suitably sulfuric acid. Contents of the urine are then oxidized by mixing the urine with a saturated solution of potassium permanganate in water until the violet color of potassium permanganate disappears. After oxidation, the treated urine is filtered and the clear filtrate is separated by C-18 chromatography performed in the same manner as described for the isolation of antineoplaston fraction A2.

The colored band visible on the column is designated fraction U and is eluted with methanol and evaporated to dryness or freeze dried. This fraction called antineoplaston fraction A4 is suitable for pharmaceutical application in the same variety of pharmaceutical formulations and routes of administration as described for antineoplaston fraction A1.

E. Isolation and Purification of Antineoplaston Fraction A5 from Human Urine The prefiltration, ultrafiltration, and acidification of reconstituted or fresh urine is repeated as described above for the preparation of antineoplaston fraction A1. The acidified material is filtered again through a $0.2\mu$ filter to remove any precipitated or sedimented residue. This filtrate is then introduced to a chromatographic column filled with C-18 bonded phase type silica gel, (available for example from Waters Associates or Whatman). Other silica gel, packings having the same physicochemical properties may be substituted for the C-18 column packing.

The column is initially washed with deionized; distilled water and then eluted with methanol. A colored methanolic fraction is collected, which is evaporated to dryness or freeze dried. The dry fraction is labelled antineoplaston fraction A5. Antineoplaston A5 is suitable for pharmaceutical application in the same variety of formulations and routes of administration as described for antineoplaston fraction A1.

F. Chromatographic Characterization of Antineoplaston Fractions A1–A5

The purposes of identifying each of the derived antineoplaston fraction, a chromatographic fingerprint was developed. Each of the derived antineoplaston fractions from the respective above-described processes was subjected to high performance liquid chromatography, a Waters Prep 500 HPLC system equipped with a Prep 500 C-18 bonded phase type silica gel column and refractive index detector. Each antineoplaston fraction was developed according to the same sequential wash routine. First, a predetermined amount of reconstituted antineoplaston fraction was introduced to the column. Typically the antineoplaston fraction in powdered form was reconstituted with distilled water.

Following introduction of the antineoplaston fraction sample, a first wash with 1000 ml of water was passed through the column. This water wash was followed with 1000 ml of an acetic acid solution, pH 2.5, wash. Finally, 1000 ml of water was passed through the column and 600 ml of methanol. As the eluates exited the column, the detector measured and recorded the apparent refractive index of the components eluted within a exiting solvent.

With reference to the figures, a characteristic chromatograph for each of the antineoplaston fractions is illustrated. The figures illustrate the relative refractive index corresponding to components present in the eluates exiting the column at the relative elution volumes, corresponding to passage of each of the solvent washes. It will be appreciated by those familiar with chromatographic development, that each chromatograph represents a resolution of peak distribution characteristic for a particular mixture. A chromatograph serves as a fingerprint analysis of the mixture or in this instance a fingerprint for the antineoplaston fractions. It is therefore apparent, that the respective product antineoplaston fractions purified according to the methods of the invention, will exhibit the characteristic chromatograph corresponding to the figures illustrated herein when developed according to the conditions described above. It will also be appreciated by those skilled in the art of chromatography, that the relative height of the peaks will vary with the concentration of the component elements present in each fraction, however, the distribution of the peaks will not vary substantially from batch to batch of each fraction.

Figure 1:
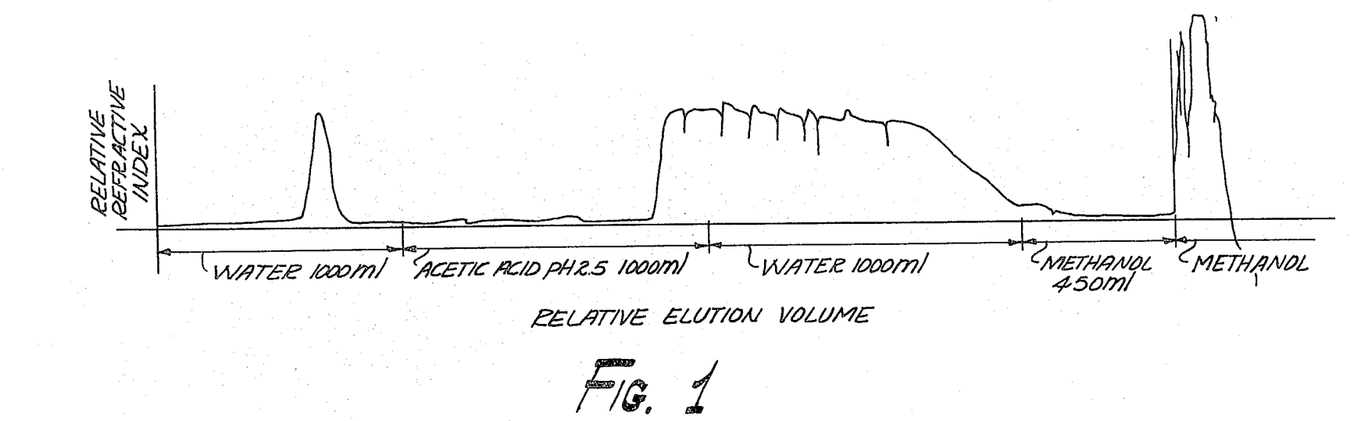
FIG. 1 represents a chromatograph of antineoplaston fraction A1.

Referring now to FIG. 1, a chromatograph is depicted wherein antineoplaston fraction A1 exhibits a discrete sharp peak in the region of first water wash. Further, antineoplaston fraction A1 exhibits a broad peak distribution comprising a series of moderately defined peaks concentrated in the region of the end of acetic acid wash and of the second water wash. In addition there are sharply defined peaks occurring after 450 ml of methanol wash.

Figure 2:
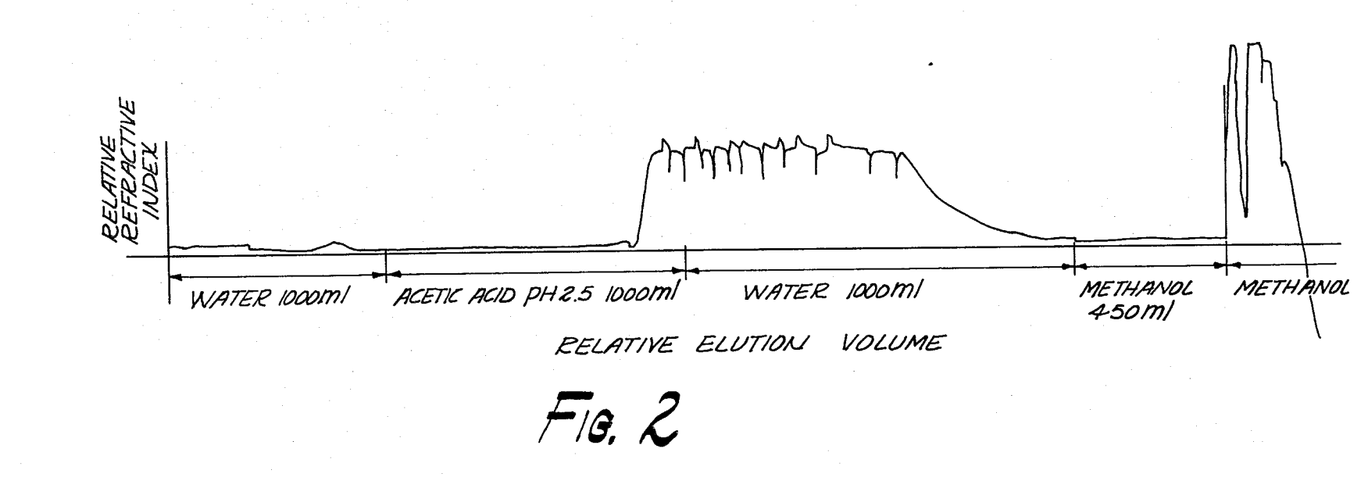
FIG. 2 represents a chromatograph of antineoplaston fraction A2.

FIG. 2 depicts the chromatograph of antineoplaston fraction A2, wherein a series of sharply defined peaks are apparent in the region of the end of acetic acid wash and extend into the region of the second water wash. Further, there are sharply defined peaks in the methanol wash.

Figure 3:
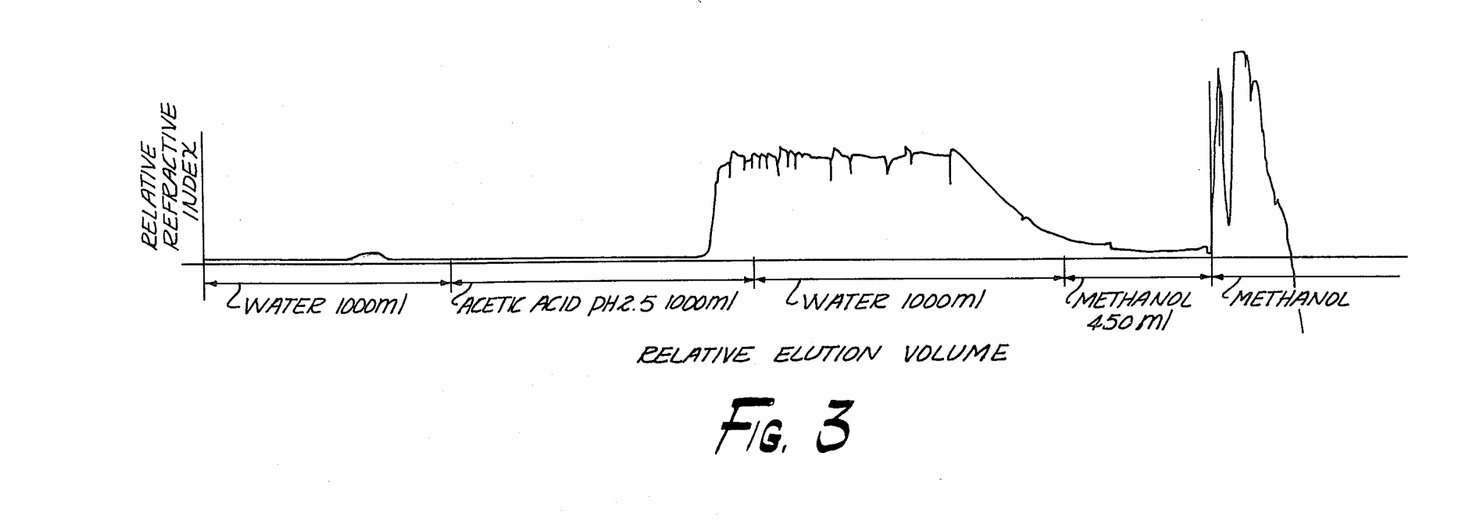
FIG. 3 represents a chromatograph of antineoplaston fraction A3.

FIG. 3 depicts the chromatograph of antineoplaston fraction A3, which exhibits a small peak in the initial water wash and a concentrated band of peaks in the region of the end of acetic acid wash and extending into the second water wash. In addition, there are well defined peaks in the methanol wash.

Figure 4:
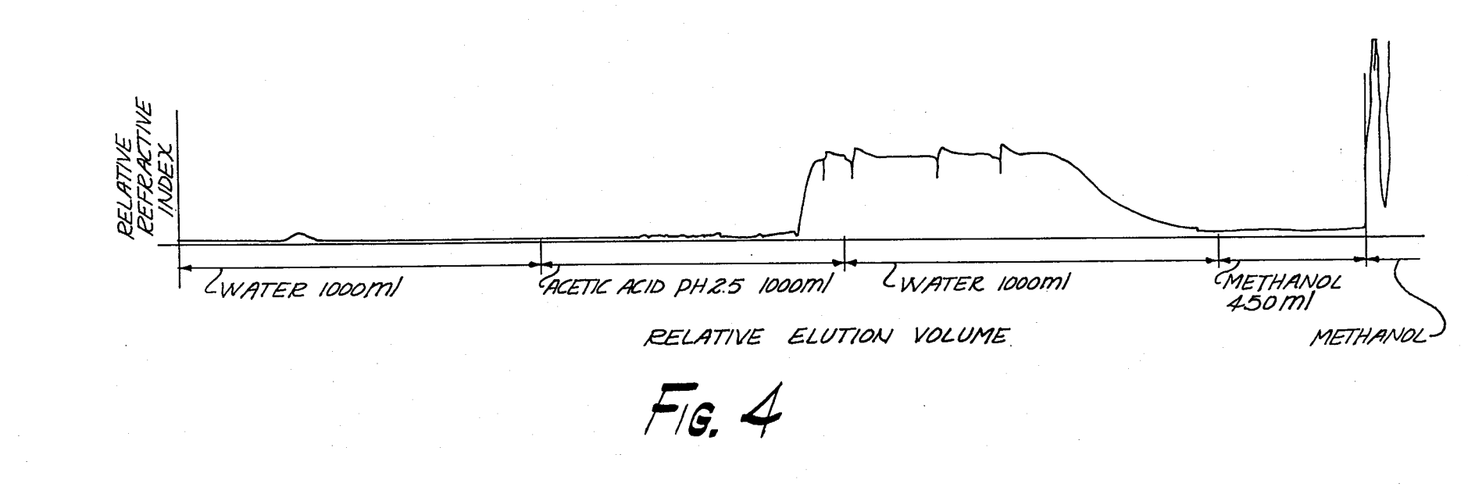
FIG. 4 represents a chromatograph of antineoplaston fraction A4.

Referring now to FIG. 4, there is depicted a chromatograph of antineoplaston fraction A4 which exhibits a small peak in the initial water wash and a broad peak resolved in the acetic acid wash and second water wash. Further, there are sharp peaks in the methanol wash.

Figure 5:
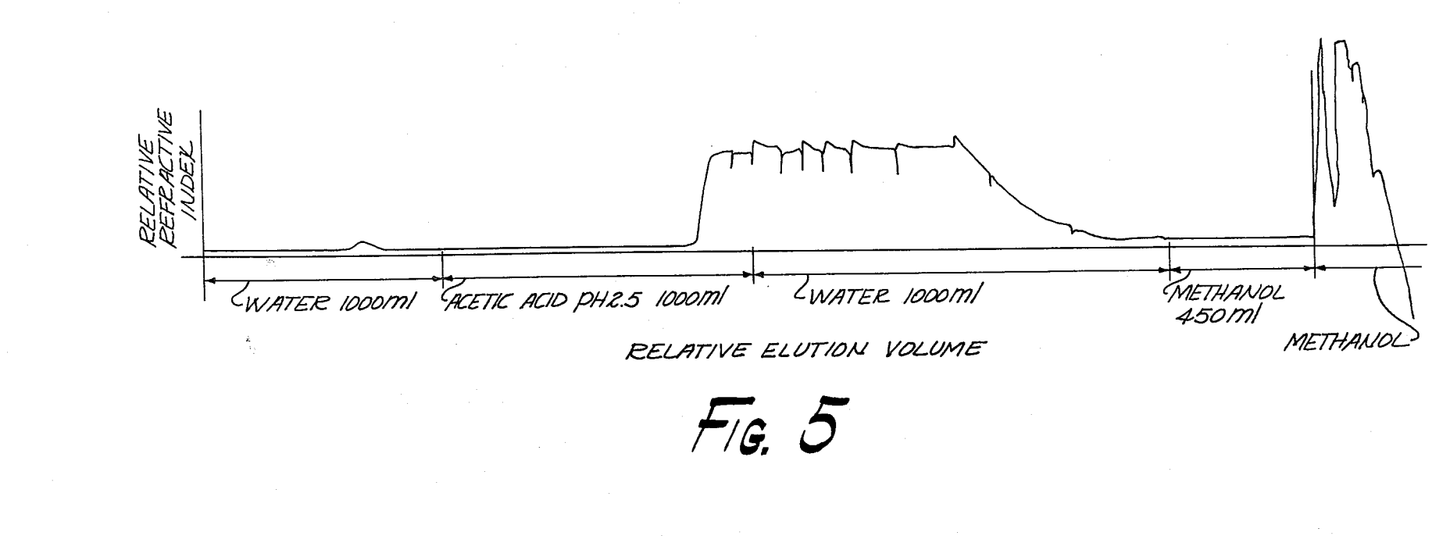
FIG. 5 represents a chromatograph of antineoplaston fraction A5.

Next, turning to FIG. 5, there is a chromatograph of antineoplaston fraction A5. The chromatograph depicts a small peak in the initial water wash and a broad peak comprising a series of moderately defined peaks in the end of acetic acid wash and extending into the second water wash. There are also well defined peaks in methanol wash.

Further attempts were made to isolate and identify the component elements of each antineoplaston fraction. The component elements of antineoplaston fractions A1–A5 were separated by high performance liquid chromatography on a column packed with sulfonated polystyrene. A system developed by Glenco Scientific Inc. for amino acid analysis was used. The elution was effected by 0.2M citrate buffers at three different values of pH, namely 3.25, 3.80 and 4.10 and at temperatures from 50° C. to 70° C. The changes of buffers and temperature were selectively controlled according to Glenco Scientific, Inc. program for amino acid analysis.

The eluates were reacted as they came off the column with ninhydrin at 110° C. to yield absorption peaks stimultaneously measured and recorded at 570 m$\mu$ and 440 m$\mu$. In order to standardize the procedure, a mixture of 18 amino acids was separated establishing the retention times presented in Table 1.

TABLE 1

| Standard Retention Times of Amino Acids | |
|---|---|
| Amino Acids | Retention Times (minutes) |
| Aspartic Acid | 18.0 |
| Threonine | 21.5 |
| Serine | 22.7 |
| Glutamic acid | 26.0 |
| Proline | 30.0 |
| Glycine | 38.4 |
| Alanine | 38.9 |
| Cysteine | 42.0 |
| Valine | 47.0 |
| Methionine | 49.0 |
| Isoleucine | 52.2 |
| Leucine | 53.8 |
| Tyrosine | 59.2 |
| Phenylalanine | 64.0 |
| Lysine | 72.0 |
| Ammonia | 78.0 |
| Histidine | 80.2 |
| Arginine | 93.5 |

Each of the antineoplaston fractions A1–A5 were separated into discrete homogeneous components under the same conditions as the standardized amino acid mixture. Table 2 summarizes the retention times of the discrete components making up each of the heterogeneous antineoplaston fractions.

TABLE 2

| Retention Time of Alpha-Amino Components of Antineoplaston Fractions A1–A5 | | | | | |
|---|---|---|---|---|---|
| Retention Time (min.) | Antineoplaston Fraction (mM/L of alpha-amino nitrogen) | | | | |
| | A1 | A2 | A3 | A4 | A5 |
| 10 | 0.12 | 1.57 | 0.24 | 1.97 | 0.20 |
| 15 | 0 | 0.78 | 0.05 | 0.82 | 0 |
| 26 | 0 | 0.22 | 0 | 0.75 | 0.13 |
| 37 | 2.44 | 0.25 | 0 | 0.59 | 0.08 |
| 48 | 0.12 | 0.47 | 0.30 | 0.77 | 0.20 |
| 53 | 0 | 0.12 | 0.04 | 0.43 | 0 |
| 63 | 0 | 0.23 | 0 | 0.63 | 0.10 |
| 71 | 0 | 0.17 | 0.07 | 0.30 | 0 |
| 76 | 0.13 | 0.14 | 0.45 | 0.87 | 0.13 |
| 79 | 39.50 | 9.39 | 4.44 | 16.35 | 14.88 |
| 82 | 0.22 | 1.01 | 0.92 | 1.09 | 0.21 |
| 85 | 0.07 | 0.62 | 0.65 | 0.45 | 0.14 |
| 101 | 0 | 0.01 | 0 | 0.10 | 0 |

The preparations of antineoplaston fractions A1, A2, A3, A4 and A5 do not contain either amino acids or proteins. The peaks recorded during analysis of the antineoplaston fractions correspond to the different compounds reacting with ninhydrin, namely amino acid derivatives and peptides. As denoted in Table 2, the relative concentration of each component compound within the particular antineoplaston fraction is measured relative to the reactivity between ninhydrin and the alpha-amino nitrogen of the component compound. In accordance with the chromatographic analysis described in this section, each antineoplaston fraction exhibits a significantly prominent peak at a retention time corresponding to 79 minutes. Further, in accordance with the methods of preparing each antineoplaston fraction embodied by the present invention, the relative concentration of the component corresponding to a 79 minute retention time is at least two times the relative concentration of any other residual component compound. It is to be appreciated, however, that the relative concentration of each component compound constituting an antineoplaston fraction will vary with the source of urine. Indeed, depending on the source of urine several of the component compounds within an antineoplaston fraction might not be evident. Applicant makes no representation that each component compound within an antineoplaston fraction possesses antineoplaston activity; rather, antineoplastic activity has been demonstrated for each antiplaston fraction A1–A5 and for the component compound characterized by a 79 minute retention time obtained by the above-described separation technique.

The major common active component of antineoplaston fraction A1, A2, A3, A4 and A5 was finally purified by high performance liquid chromatography and thin layer chromatography. Applicant has termed this compound antineoplaston A10. Its chemical structure was determined by mass spectrometry, 13c(NMR) spectroscopy, and infrared spectrometry. The structure is depicted below and termed 3-[N-phenylacetylaminopiperidine]-2, 6-dion.

G. Synthesis of Antineoplaston A10, 3-[N-phenylacetylaminopiperidine]-2, 6-dion Sodium bicarbonate (4.7 mole) and L-glutamine (2.3 mole) were dissolved in water (13.5 liters). Phenylacetyl chloride (3.0 mole) was gradually added to the reaction mixture and vigorously stirred for 90 minutes. After completed reaction, the pH of the solution was adjusted to 2.5 with acid and the solution filtered. The filtrate was extracted twice with dichloromethane and the lower organic layers were discarded. The upper aqueous layer had the pH adjusted to 7.0 with base, typically 1N NaOH. The upper layer was then further purified by mixing with Norit A (20 g) (available from American Norit Co., Jacksonville, Fla.). The mixture was filtered after 30 minutes contact with Norit A. The resultant filtrate was evaporated and the residue redissolved in methanol. The recovered methanolic solution was filtered and freeze dried or evaporated. The dried residue was redissolved in water and the pH adjusted to 2.5 suitably with HCl. Two layers were formed after standing at room temperature. The lower layer was heated until it turned dark brown. This viscous brown layer was redissolved in methanol wherein crude antineoplaston A10 precipitated upon cooling. The crude antineoplaston A10 was redissolved in hot methanol and Norit A was added to remove any color. The solution was filtered while hot. On cooling, white crystals of antineoplaston A10 formed. The structure of the synthetic material was elucidated by mass spectrometry, 13c(NMR) spectroscopy and infrared spectrometry and was found to be identical to the major common active component of antineoplaston fractions A1, A2, A3, A4 and A5 having a 79 minute retention time.

Antineoplaston A10 is most suitable for pharmaceutical applications in the form of salts, sodium salt being preferred. In order to prepare sodium salt, antineoplaston A10 is suspended in ethanol and heated with a solution of sodium hydroxide in water until all material is dissolved. The reaction mixture is then freeze dried. The solid residue is kept at room temperature until the salt crystallizes out. Ethanol is added and stirred. Filtration yields a white crystalline solid corresponding to the sodium salt of antineoplaston A10. Suitable solutions for parenteral administration are prepared by dissolving sodium salt of antineoplaston A10 in pyrogen free water up to a concentration of 100 mg/ml and adjusting the pH to 7.0.

H. Degradation Products of Antineoplaston A10

The initial hydrolysis of antineoplaston A10 yields phenylacetyl glutamine, and when carried further produces phenylacetic acid:

3-[N—phenylacetylaminopiperidine]-2,6-dion

N—phenylacetyl glutamine

Phenylacetic acid    Glutamine

Phenylacetyl glutamine was first described by Thierfelder and Sherwin [see *J. Physiol. Chem.* 94:1 (1915)] as a constituent of normal human urine. In later investigations of the compound phenylacetyl glutamine was shown to have a slight effect on the growth of murine tumors [see Lichtenstein et al, *Isreal J. Med. Sci.*, 13:316 (1977)] but there was no indication that the compound was useful in the treatment of human cancer. The sodium salt of phenylacetic acid was used by Neish in the treatment of Rd/3 sarcoma in rats but failed to inhibit tumor growth. Indeed, the results suggested that the treatment with phenylacetic acid caused some enhancement of tumor growth [see Neish, *Experientia*, 27:860 (1971)]. Applicant has demonstrated in his clinical studies that phenylacetyl glutamine alone and a mixture of phenylacetyl glutamine and phenyl acetic acid are each useful in the treatment of human cancers.

A mixture of the sodium salts of phenylacetyl glutamine and phenyl acetic acid in the ratio of 1 to 4 is the preferred formulation for use in the treatment of human cancer.

Solutions for parenteral administration are prepared by reconstituting the respective chemicals in form of sodium salts in pyrogen free water to the desired total concentration, for example 100 mg/ml. The pH of the solution is adjusted to 7.0 with 1N NaOH or 1N HCl. Sterilization of the reconstituted solution is done by filtration according to the guidelines of the U.S. Pharmacopeia. The sterility of the material is tested as required by the rules and regulations of the Food and Drug Administration, Section 610.12. The resulting sterile formulations are suitable for parenteral injections.

I. Pharmaceutical Applications for Antineoplaston Fractions A1–A5, Antineoplaston A10, and Degradation Products Solutions for parenteral administration are prepared by reconstituting each respective antineoplaston fractions, antineoplaston A10 and degradation products in pyrogen free water to a desired convenient concentration, for example, 100 mg/ml. The pH of the solution is adjusted to 7.0 with 1N HCl or 1N NaOH.

Sterilization of the reconstituted solution is done by filtration according to the guidelines of the *U.S. Pharmacopeia.* Alternatively, the lyophilized powders of the respective antineoplaston fractions can first be gas sterilized, for example with ethylene oxide, and the powders subsequently incorporated into the pyrogen free water which, of course, itself is sterile. The sterility of the material is tested as required by the Rules and Regulations of the Food and Drug Administration, Section 610.12. The resulting sterile formulations are suitable for intravenous, intramuscular, subcutaneous, intracavital and intratumor injection.

If the reconstituted lyophilized antineoplaston fraction is not to be used immediately, the prevention of microbial proliferation can be attained by the addition of various antibacterial and antifungal agents to the antineoplaston solutions, for example, parabens, chlorobutanol, benzyl alcohol, phenol, sorbic acid, thimerosal, and the like. In many instances it will be desirable to include isotonic agents to the injectable solutions, for example, sugars or sodium chloride.

The antineoplastic activity of the antineoplaston fractions A1–A5, antineoplaston A10 and degradation products was first evaluated experimentally by observing the cytostatic effects the preparations would have on a tumor line as compared to the overall toxicity the preparation would have on experimental animals. Accordingly, the preparation having the greatest cytostatic activity and the lowest animal toxicity are said to have the better antineoplastic activity, or therapeutic effectiveness.

The cytostatic activity of antineoplaston fraction A1 was tested in a culture of human carcinoma of the breast line MDA-MB-231 obtained from M. D. Anderson Cancer Institute, Houston, Tex. MDA-MB-231 is a fast growing line of human breast cancer established by Cailleau et al, *J. Natl. Cancer Inst.*, 53:661 (1974). The estimated doubling time of these cells is 18 hours when grown in the original medium described by Beall et al, *Physiol. Chem. Physics,* 8:281 (1976). Briefly, to summarize the preferred medium and method, the cells are grown in monolayers at 37° C. in Leibovitz L-15 medium supplemented with 20% fetal bovine serum, 1.6 µg/ml glutathione, 0.25 U/ml insulin, 100 µg/ml disodium carbenicillin and 100 µg/ml gentamycin.

For the bioassay, antineoplaston fraction A1 was dissolved in the above-described medium at four different concentrations selected arbitrarily with the range of 0.5 to 50 mg/ml. Monolayer cultures were incubated with the antineoplaston fraction A1-containing medium for 96 hours. The cells were counted by visual method at 24 hour intervals. Control cultures were grown in the standard medium without added antineoplaston fraction A1.

Antineoplaston fraction A1 in concentrations of 5 mg/ml produces a cytostatic effect in such human breast carcinoma cultures. The cytostatic effect is determined as a stable number of cells (within the limits from 80% to 120%) counted after 24 hours from incubation and persisting for at least an additional 48 hours.

The cytostatic concentration of the antineoplaston fraction A2–A5 and antineoplaston A10 and degradation products were determined in the same manner described above. The cytostatic concentration for each antineoplaston fraction is as follows:

| Antineoplaston | Cytostatic Concentration |
|---|---|
| Fraction A1 | 5 mg/ml |
| Fraction A2 | 5 mg/ml |
| Fraction A3 | 5 mg/ml |
| Fraction A4 | 2 mg/ml |
| Fraction A5 | 2 mg/ml |
| A10 | 2 mg/ml |
| Phenyl acetyl glutamine | 10 mg/ml |
| Phenyl acetyl glutamine and Phenyl acetic acid (1:4 mixture) | 3 mg/ml |

Above these concentrations all antineoplaston fractions produce cytotoxic effect in human breast carcinoma cultures.

Acute toxicity studies on experimental animals reveal that antineoplaston fraction A1 has very low toxicity. For example, experiments involving twenty-five HA-/ICR swiss mice injected intraperitoneally with antineoplaston fraction A1 resulted in a $LD_{50}$ of 1.35 g/kg. The autopsy and microscopic studies of the tissues of the animals which died during the experiment revealed congestion of the liver and marked pulmonary edema. The animals which survived were kept for one week under close observation and were noted to carry on normal activity. After a week, a select number of the mice were sacrificed. The autopsy and microscopic examination of the tissues of these animals were identical to those of control, uninjected subjects.

Acute toxicity studies involving antineoplaston fractions A2–A5, antineoplaston A10 and degradation products were carried out in the same manner described above. The respective $LD_{50}$ for mice for each fraction is as follows:

| Antineoplaston | $LD_{50}$ |
|---|---|
| Fraction A1 | 1.35 g/kg |
| Fraction A2 | 3.55 g/kg |
| Fraction A3 | 3.55 g/kg |
| Fraction A4 | 5.33 g/kg |
| Fraction A5 | 5.11 g/kg |
| A10 | 10.33 g/kg |
| Phenyl acetyl glutamine | 2.90 g/kg |
| Phenyl acetyl glutamine and Phenyl acetic acid (1:4 mixture) | 2.83 g/kg |

J. Clinical Evaluation of Antineoplaston

The definitions of remission associated with neoplastic disease are as follows: complete remission is the disappearance of all clinical evidence of diseases and partial remission is reduction by at least 50% in the sum of the products of two perpendicular diameters of all measurable disease lasting at least four weeks. Patients are considered stabilized if measurable tumor regression occurs but does not meet the criteria for partial remission.

In accordance with the methods in the present invention, human neoplastic disease was treated with the various antineoplaston fractions. For each neoplastic disease studied, each tested antineoplaston fractions, antineoplaston A10 and degradation product, phenylacetyl glutamine, and a combination of phenylacetyl glutamine and phenylacetic acetic was effective to some extent in aiding the regression of tumors. As would be expected, some fractions or compositions exhibited more effectiveness for some forms of neoplasia than other fractions.

The dosage of the selected antineoplaston fraction for the treatment of the indicated neoplastic condition depends on the age, weight and condition of the patient; the particular neoplastic disease and its severity; and the route of administration. A dose of from about 0.5 to about 12 g/m$^2$/24 hr. or a total dose of from about 0.9 to about 20 g given in divided doses of up to 6 times a day embraces the effective range for the treatment of most neoplastic conditions for any one of antineoplaston fractions A1–A5, antineoplaston A10, and degradation products.

EXAMPLE I

To date, fourteen patients with advanced cancer have been treated with antineoplaston fraction A2 and followed for up to one year. The preferable route for the administration of the preparation is intravenous injection given every 12 hours through a catheter inserted into the subclavian vein. Direct intrapleural or intraperitoneal injections can also be given. The average dose given was 0.85 g/m$^2$ and the maximum was 2.2 g/m$^2$ intravenously every 12 hours. Full dose intravenous treatment with antineoplaston fraction A2 was usually given until the complete remission was obtained and then continued for at least 6 weeks to eradicate any remaining microscopic disease. Afterwards, IV injections were discontinued and the maintenance treatment was started. Maintenance treatment consisted of IM injections of 2 to 3 ml of 50 mg/ml antineoplaston fraction A2 initially given every other day. If no sign of cancer recurred, the frequency of IM injections was reduced every 6–8 weeks, tapering from one injection every third day to one injection once a week.

In the group of 14 patients treated with antineoplaston fraction A2 four obtained complete remission. These four cases included undifferentiated large cell carcinoma of the lung, stage III (T3NOMO); poorly differentiated metastatic carcinoma of the liver with unknown primary; and two cases of recurrent transitional cell carcinoma of the bladder, grade II. In an additional case involving adenocarcinoma of the breast with multiple bone and liver metastases, stage IV (TONOMIOSS, HEP) a complete remission of large liver metastases and stabilization of bone metastases was obtained. There was also one additional case of transitional cell carcinoma of the bladder, grade II in which complete remission was obtained with help of antineoplaston fraction A2. In this case antineoplaston fraction A2 was given as a maintenance treatment after the complete remission was obtained with antineoplaston A.

Partial remission was obtained in three cases: peritoneal mesothelioma; carcinoma of the breast with multiple bone metastases, stage IV, TONOMIOSS; and squamous cell carcinoma of the esophagus with multiple lung metastases, stage III, T3NOMIPUL.

Stabilization of the disease was obtained in four cases which included glioma, stage IV; adenocarcinoma of the kidney with multiple lung metastases; carcinoma of the breast with multiple bone metastases, stage IV, TONOMIOSS; and carcinoma of the breast with lymph node involvement, stage IV, TON3MO.

Overall response rate to the treatment with antineoplaston fraction A2 is 93% with only one patient (7%) showing continued progressive disease. The treatment is very well tolerated. Few side effects were evident including stimulation of the growth of epidermis, stimulation of bone marrow and very infrequent fever. Stimulation of the growth of epidermis was evident after 3 weeks of treatment as more rapid growth of nails and a thicker skin on the palms. Stimulation of the bone marrow was shown as elevated white blood and platelet count. These side effects are beneficial in most cases because of poor healing of the skin and myelosuppression present in large number of cancer patients.

EXAMPLE II

The following case history illustrates a successful method of treatment employing antineoplaston fraction A3 for the treatment of adenocarcinoma of the prostate with bone metastases, stage IV (RONOMIOSS, G3).

Treatment of a 72 year old white male was initiated with antineoplaston A (see Burzynski et al, *Physiol. Chem. Phys.* 9:485, 1977) for three months. The initial treatment with antineoplaston A resulted in the stabilization of the disease and some questionable decrease of the size of the metastases.

After three months antineoplaston A was discontinued and the patient was started on antineoplaston fraction A3. He received a first injection of 1 ml of antineoplaston fraction A3, 100 mg/ml given through a subclavian catheter followed with 3 ml of normal saline and 250 units of heparin. The dose was further increased up to 5 ml of the same preparation given intravenously every 12 hours. Such a treatment regimen corresponds to the dosage 0.47 g/m$^2$/24 hour. After approximately 7 months the frequency of the injections was decreased to 2 ml of antineoplaston fraction A3, 100 mg/ml, given intramuscularly every third day, and finally after 4 months the dosing regimen was further decreased to 2 ml of the preparation administered intramuscularly once a week.

The treatment with antineoplaston fraction A3 resulted in the complete remission of the bone metastastes as judged by bone scans. The treatment was very well tolerated without any apparent side effects.

Patient is continuing a maintenance treatment with antineoplaston fraction A3, and has not shown any recurrence of his cancer at the present time.

EXAMPLE III

Phenyl acetyl glutamine in the form of its sodium salt was given in two routes of administration-intravenous and oral. The observed effective dosage range was between 1.1 g/m$^2$/24 h to 3.0 g/m$^2$/24 h IV and 0.5 g/m²/24 h to 2.8 g/m²/24 h po. The intravenous injections were usually given in divided doses preverably every 6 hours. Oral preparations were given in the form of 500 mg capsules every 12 or every 6 hours. Six patients were treated with the sodium phenyl acetyl glutamine. Complete remission was obtained in two cases which included squamous cell carcinoma of the larynx, stage II and large cell undifferentiated carcinoma of the lung with lymph node and liver metastases, stage III. Stabilization of the disease was observed in one case of adenocarcinoma of the lung, stage III. Progression of the disease was noticed in three patients who were suffering on adenocarcinoma of the sigmoid colon with multiple liver metastases, stage IV and adenocarcinoma of the colon with multiple metastases, stage IV and carcinoma of the breast with multiple lung and bone metastases, stage IV. The treatment was usually started with intravenous injections and continued until complete remission was obtained. Afterwards, the maintenance treatment was implemented by using the oral preparation. Oral administration of phenyl acetyl glutamine sodium salt often produced mild irritation of the stomach, which was relieved by the concomitant administration of antacids preparations.

EXAMPLE IV

In clinical studies involving the therapeutic assessment of phenyl acetyl glutamine and phenyl acetic acid a 1:4 mixture of sodium salts was selected as the base formulation. This mixture reconstituted in sterile, buffered water was primarily administered through the intravenous route in the dose range from 0.24 g/m²/24 hr. to 5.3 g/m²/24 hr. The daily amount was usually given in divided doses preferably every 6 hours. Ten patients with various advanced neoplastic conditions were evaluated.

There was only one case in which complete remission was obtained but the phenyl acetyl glutamine and phenyl acetic acid mixture was used after patient received radiation. Therefore the beneficial effect of the treatment could be due to the combination effect from radiation and chemotherapy. This patient was suffering on carcinoma of the uterine cervix, stage 1A. There were four cases of partial remission obtained during the treatment with the mixture. In three of these cases there was no other conventional treatment given in addition to the mixture. These cases included: carcinoma of the breast with multiple bone metastases, stage IV, lymphocytic lymphoma, stage IV, and chronic myelocytic leukemia. In an additional case of adenocarcinoma of the lung with multiple brain metastases, stage III the treatment with phenyl acetyl glutamine and phenyl acetic acid mixture was given after radiation therapy. Stabilization of the disease was seen in three cases which included carcinoma of the sigmoid colon with multiple liver metastases, stage IV, glioma (primary malignant brain tumor) and carcinoma of the larynx with multiple lung metastases, stage IV.

Implementation of the disclosed antineoplaston fractions A1-A5, antineoplaston A10, phenylacetyl glutamine and a combination of phenylacetyl glutamine and phenylacetic acid has been directed with success in the regression of tumors associated with human cancer of esophagus, breast cancer, bladder cancer, colon cancer, large cell undifferentiated carcinoma of the lung, mesothelioma, adenocarcinoma and squamous cell carcinoma of the lung, oat cell carcinoma, brain metastases, bone metastases, lung metastases, prostate cancer, pancreas cancer, lymphatic lymphoma, uterine cervix cancer, primary malignant brain tumor.

Further, each of the antineoplaston fractions A1-A5, antineoplaston A10, phenylacetyl glutamine, and combinations of phenylacetyl glutamine and phenylacetic acid are useful in the treatment of other forms of neoplastic disease including myelocytic leukemia, cancer of the larynx, cancer of the uterus, lymphoma, cancers of the colon and sigmoid.

The foregoing description of the invention has been directed to particular examples of the extraction of antineoplastic peptide fractions from human urine for purposes of explanation and illustration. It is to be understood however, that many modifications and changes in the product compositions, the processes for extracting the antineoplaston fractions, the synthesis of antineoplaston A10, and methods of using the same can be made in the implementation and utilization of the present invention without departing from the scope of invention defined in the claims. For example, it is contemplated that peptides having antineoplastic activity can be extracted from sources other than urine, such as, blood, saliva, organ or tissue samples. It is to be understood that Applicant has directed his fractionation processes to urine based on the economic feasibility of obtaining a large volume of the fluid which is necessary to derive usable amounts of the antineoplaston fraction normally present in such fluid at very low concentration. However, it will be appreciated by those skilled in the art after considering this specification that other tissue fluids or tissue samples also contain minute amounts of peptides exhibiting antineoplastic activity, and that such peptides can be extracted by modification of the processes described herein.

What is claimed is:

1. A process for extracting from urine a peptide fraction containing the compound 3-[N-phenylacetylaminopiperidine]-2, 6-dion comprising the steps of:
   providing a volume of urine;
   separating from the urine particulate matter and matter having a molecular weight greater than from about 5000;
   acidifying the urine;
   separating from the acidified urine any precipitated matter;
   introducing the acidified urine to a chromatography column; and
   recovering the cytostatic active peptide fraction, said peptide fraction containing the compound 3-[N-phenylacetylaminopiperidine]-2, 6-dion.

2. The process of claim 1 wherein the urine is acidified to a pH ranging from about 2 to about 3.

3. The process of claim 1 wherein the urine is acidified to about pH 2.5.

4. The process of claim 1 wherein the acidified urine is introduced to a high performance liquid chromatography column.

5. The process of claim 4 wherein the high performance liquid chromatography is conducted on C-18 bonded phase silica gel.

6. The process of claim 1 which further comprises:
   purifying from the peptide fraction the compound 3-[N-phenylacetylaminopiperidine]-2, 6-dion.

7. The process of claim 6 wherein the purification is accomplished by a second high performance liquid chromatography operation.

8. The process of claim 7 wherein the second high performance liquid chromatography operation is conducted on sulfonated polystyrene according to the Glenco Scientific, Inc., system for amino acids, or an equivalent system.

9. A product made in accordance with the process of claim 1.

10. A product made in accordance with the process of claim 1 having a characteristic chromatograph shown in FIG. 1 of the drawings wherein the chromatograph represents the refractive index pattern of peaks developed by high performance liquid chromatography conducted on a C-18 bonded phase type silica gel after sequential washings with a first wash of about 1000 ml of water; a second wash with about 1000 ml acetic acid solution; a third wash with about 1000 ml of water; and a final wash with 600 ml of methanol.

11. A process for extracting from urine a peptide fraction containing the compound 3-[N-phenylacetylaminopiperidine]-2, 6-dion comprising the steps of:
providing a volume of urine;
separating from the urine particulate matter and matter having a molecular weight greater than about 5000;
acidifying the urine;
separating from the acidified urine any precipitated matter;
introducing the acidified urine to a first chromatography column containing a polymeric resin adsorbent;
eluting the column to recover an eluate;
adjusting the pH of the eluate to between about 2 and 8;
introducing the adjusted eluate to a second chromatography column; and
recovering the cytostatic active peptide fraction, said peptide fraction containing the compound 3-[N-phenylacetylaminopiperidine]-2, 6-dion.

12. The process of claim 11 wherein the column is eluted with water, alcohol, or mixtures of both.

13. The process of claim 11 wherein the second chromatography column contains C-18 bonded phase silica gel.

14. The process of claim 11 wherein the urine is acidified to a pH ranging from about 1 to about 2.

15. The process of claim 11 wherein the urine is acidified to about pH 1.5.

16. The process of claim 11 wherein the polymeric resin adsorbent is Amberlite XAD-8.

17. The process of claim 11 wherein the pH of the eluate is adjusted to about pH 2.5.

18. The process of claim 11 which further comprises:
purifying from the peptide fraction the compound 3-[N-phenylacetylaminopiperidine]-2, 6-dion.

19. The process of claim 18 wherein the purification is accomplished by a high performance liquid chromatography operation.

20. The process of claim 19 wherein the high performance liquid chromatography operation is conducted on sulfonated polystyrene according to the Glenco Scientific, Inc., system for amino acids.

21. The product made in accordance with the process of claim 11.

22. The product made in accordance with process of claim 11 having a characteristic chromatograph shown in FIG. 2 of the drawings wherein the chromatograph represents the refractive index pattern of peaks developed by high performance liquid chromatography conducted on a C-18 bonded phase type silica gel after sequential washings with a first wash of about 1000 ml of water; a second wash with about 1000 ml acetic acid solution, pH 2.5; a third wash with about 1000 ml of water; and a final wash with 600 ml of methanol.

23. A process for extracting from urine a peptide fraction containing the compound 3-[N-phenylacetylaminopiperidine]-2, 6-dion comprising the steps of:
providing a volume of urine;
separating from the urine particulate matter and matter having a molecular weight greater than about 5000;
acidifying the urine;
separating from the acidified urine any precipitated matter;
introducing the acidified urine to a first chromatography column containing a resin adsorbent;
eluting the column with an alkaline wash;
collecting the alkaline wash eluate;
adjusting the pH of the alkaline wash eluate from about pH 2 to about 8;
oxidizing the acidified eluate;
introducing the oxidized acidified eluate to a second chromatography column; and
recovering the cytostatic active peptide fraction, said peptide fraction containing the compound 3-[N-phenylacetylaminopiperidine]-2, 6-dion.

24. The process of claim 23 wherein the acidified eluate is oxidized before introducing the eluate to the second chromatography column.

25. The process of claim 23 wherein the second chromatography column contains C-18 bonded phase silica gel.

26. The process of claim 23 wherein the urine is acidified to a pH ranging from about 1 to about 2.

27. The process of claim 23 wherein the urine is acidified to about pH 1.5.

28. The process of claim 23 wherein the polymeric resin adsorbent is Amberlite XAD-8.

29. The process of claim 23 wherein the pH of the alkaline wash eluate is adjusted to a pH ranging from 2 to 3.

30. The process of claim 23 wherein the resulting acidified solution is oxidized with potassium permanganate.

31. The process of claim 23 which further comprises:
purifying from the peptide fraction the compound 3-[N-phenylacetylaminopiperidine]-2, 6-dione.

32. The process of claim 31 wherein the purification is accomplished by a high performance liquid chromatography operation.

33. The process of claim 32 wherein the high performance liquid chromatography operation is conducted on sulfonated polystyrene according to the Glenco Scientific, Inc., system for amino acids.

34. A product made in accordance with the process of claim 23.

35. A product made in accordance with the process of claim 23 having a characteristic chromatograph shown in FIG. 3 of the drawings wherein the chromatograph represents the refractive index pattern of peaks developed by high performance liquid chromatography conducted on a C-18 bonded phase type silica gel after sequential washings with a first wash of about 1000 ml of water; a second wash with about 1000 ml acetic acid solution, pH 2.5; a third wash with about 1000 ml of water; and a final wash with 600 ml methanol.

36. A process for extracting from urine a peptide fraction containing the compound 3-[N-phenylacetylaminopiperidine]-2, 6-dion comprising the steps of:
providing a volume of urine;
subjecting the urine to oxidation;
adjusting the pH of the urine to between about 2 and about 8;
removing from the oxidized urine any precipitated matter;
introducing the oxidized urine to a chromatography column; and
recovering the cytostatic active peptide fraction, said peptide fraction containing the compound 3-[N-phenylacetylaminopiperidine]-2, 6-dion.

37. The process of claim 36 wherein the urine is acidified to a pH ranging from 2 to 3.

38. The process of claim 36 wherein the chromatography is conducted on C-18 bonded phase silica gel.

39. The process of claim 36 which further comprises: purifying from the peptide fraction the compound 3-[N-phenylacetylaminopiperidine]-2, 6-dion.

40. The process of claim 39 wherein the purification is accomplished by a high performance liquid chromatography operation.

41. The process of claim 39 wherein the high performance liquid chromatography operation is conducted on sulfonated polystyrene according to the Glenco Scientific, Inc., system for amino acids.

42. A product made in accordance with the process of claim 36.

43. A product made in accordance with the process of claim 36 having a characteristic chromatograph shown in FIG. 4 of the drawings wherein the chromatograph represents the refractive index pattern of peaks developed by high performance liquid chromatography conducted on a C-18 bonded phase type silica gel after sequential washings with a first wash of about 1000 ml of water; a second wash with about 1000 ml of acetic acid solution, pH 2.5; a third wash with about 1000 ml of water; and a final wash with 600 ml methanol.

44. A process for extracting from urine a peptide fraction containing the compound 3-[N-phenylacetylaminopiperidine]-2, 6-dione comprising the steps of:
providing a volume of urine;
separating from the urine particulate matter and matter having a molecular weight greater than about 5000;
acidifying the urine;
separating from the acidified urine any precipitated matter;
introducing the acidified urine to a chromatography column;
eluting the column with a lower alkyl alcohol having from 1 to 8 carbon atoms; and
recovering the cytostatic active peptide fraction, said peptide fraction containing the compound 3-[N-phenylacetylaminopiperidine]-2, 6-dion.

45. The process of claim 44 wherein the urine is acidified to a pH ranging from about 2 to about 3.

46. The process of claim 44 wherein the urine is acidified to about pH 2.5.

47. The process of claim 44 wherein the acidified urine is introduced to a high performance chromatography column.

48. The process of claim 44 wherein the high performance chromatography is conducted on C-18 bonded phase silica gel.

49. The process of claim 44 which further comprises: purifying from the peptide fraction the compound 3-[N-phenylacetylaminopiperidine]-2, 6-dion.

50. The process of claim 49 wherein the purification is accomplished by a high performance chromatography operation.

51. A product made in accordance with the process of claim 44.

52. A product made in accordance with the process of claim 44 having a characteristic chromatograph shown in FIG. 5 of the drawings wherein the chromatograph represents the refractive index pattern of peaks developed by high performance liquid chromatography conducted on a C-18 bonded phase type silica gel after sequential washings with a first wash of about 1000 ml of water; a second wash with about 1000 ml acetic acid solution, pH 2.5; a third wash with about 1000 ml of water; and a final wash with 600 ml of methanol.

* * * * *